(12) United States Patent
Levi et al.

(10) Patent No.: US 8,306,607 B1
(45) Date of Patent: Nov. 6, 2012

(54) IMPLANTABLE SENSING ARRANGEMENT AND APPROACH

(75) Inventors: Ofer Levi, Los Altos, CA (US); Evan P. Thrush, San Francisco, CA (US); James S. Harris, Stanford, CA (US); Stepehn J. Smith, Los Altos, CA (US); Krishna V. Shenoy, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1453 days.

(21) Appl. No.: 10/979,091

(22) Filed: Nov. 1, 2004

Related U.S. Application Data

(60) Provisional application No. 60/515,782, filed on Oct. 30, 2003.

(51) Int. Cl.
*A61B 5/00* (2006.01)
(52) U.S. Cl. ........................ 600/473; 600/476
(58) Field of Classification Search .................... 600/473
See application file for complete search history.

(56) References Cited

U.S. PATENT DOCUMENTS

| | | | |
|---|---|---|---|
| 5,122,974 A * | 6/1992 | Chance | 600/323 |
| 5,820,558 A * | 10/1998 | Chance | 600/473 |
| 5,914,976 A | 6/1999 | Jayaraman et al. | |
| 5,936,730 A | 8/1999 | Foley et al. | |
| 5,954,053 A * | 9/1999 | Chance et al. | 600/310 |
| 5,978,401 A | 11/1999 | Morgan | |
| 6,097,748 A | 8/2000 | Huang et al. | |
| 6,197,503 B1 | 3/2001 | Vo-Dinh et al. | |
| 6,272,367 B1 | 8/2001 | Chance | |
| 6,344,644 B1 | 2/2002 | Minakuchi | |
| 6,379,969 B1 | 4/2002 | Mauze et al. | |
| 6,427,086 B1 * | 7/2002 | Fischell et al. | 607/45 |
| 6,453,183 B1 | 9/2002 | Walker | |
| 6,542,772 B1 | 4/2003 | Chance | |
| 6,560,486 B1 * | 5/2003 | Osorio et al. | 607/45 |
| 6,618,614 B1 * | 9/2003 | Chance | 600/473 |
| 6,785,568 B2 * | 8/2004 | Chance | 600/340 |
| 2002/0099295 A1 * | 7/2002 | Gil et al. | 600/476 |
| 2003/0023319 A1 * | 1/2003 | Andersen et al. | 623/24 |
| 2003/0078504 A1 | 4/2003 | Rowe | |
| 2003/0088274 A1 * | 5/2003 | Gliner et al. | 607/3 |

* cited by examiner

*Primary Examiner* — Jonathan Cwern
(74) *Attorney, Agent, or Firm* — Crawford Maunu PLLC

(57) ABSTRACT

Characteristics of biological substances, such as cerebral cortex matter, are sensed. According to an example embodiment, the present invention is directed to a negligibly-intrusive, multi-layer integrated circuit arrangement for monitoring activity of an area of a cerebral cortex that would normally be covered by an anatomical layer. The multi-layer integrated circuit arrangement includes an optics layer located outside the cerebral cortex area that includes an emitter and a detector. The optics layer is adapted for implantation in the anatomical layer and for sensing at least one brain-activity parameter. The multi-layered integrated circuit arrangement also includes a data-processing layer that includes a digital-processing circuit that is adapted for assimilating neural data in response to the optics layer sensing at least one brain-activity parameter.

1 Claim, 4 Drawing Sheets

IMPLANTABLE SENSING ARRANGEMENT AND APPROACH

RELATED PATENT DOCUMENTS

This patent document claims the benefit, under 35 U.S.C. 119(e), of U.S. Provisional Patent Application Ser. No. 60/515,782, entitled "Implantable Sensing Arrangement and Approach," and filed on Oct. 30, 2003.

FEDERALLY SPONSORED RESEARCH OR DEVELOPMENT

This invention was made with Government support under contract MDA 972-00-1-0032 awarded by the Defense Advanced Research Projects Agency. The U.S. Government has certain rights in this invention.

FIELD OF THE INVENTION

The present invention relates generally to integrated micro-circuit arrangements, and more particularly to integrated micro-circuit arrangements having a one-sided architecture for stimulating and sensing electromagnetic radiation.

BACKGROUND OF THE INVENTION

Dynamic interactions of very large neuronal population in the brain underlie our ability to generate expectations about the outcome of a future event, learn the complex laws of nature and create art. These dynamic interactions are also responsible for relatively lower-level functions, such as motor control and respiratory control, in both humans and animals. Sensory perception and higher cortical functions emerge from these intricate dynamic interactions in very large cortical network. Therefore, understanding the functioning of a cortical area requires following the dynamics of a neuronal population activity with high spatial and temporal resolution.

The basic neural research in sensing neural activity in (preferably free-behaving) animal models allows for better understanding of brain functionality. This basic research has led to continuous development of many experimental techniques where theories of brain functions can be examined in real-time by tracking neuro-physiological signals. These studies are worth pursuing not only due to their scientific merit but since they provide the foundations essential for tracking and treating in early stages of diseases. For example, motor disorders in Parkinson's disease or vision and hearing dysfunction after accidents or brain damage events may be tracked or treated using these studies. These studies are also vital to finding new ways to restore functionality for paralyzed patients.

Previously available techniques for brain interrogation include, among others, functional MRI (fMRI) and positron emission tomography (PET), as well as near-infrared spectroscopy. These techniques rely on the metabolic consequences of changes in neuronal activity and can obtain spatial resolution (below 100 microns in some cases). These methods typically monitor regional changes in cerebral blood flow and blood oxygenation level, relying on the coupling between local electrical activity and the cerebral microcirculation. However, these techniques are slow relative to the neuronal activity, which limits the ability to track neuronal signals.

Other conventional recording techniques for brain activity provide temporal resolution in the millisecond range but these techniques have undue limitations in spatial resolution. For example, electroencephalography (EEG) non-invasively records electrical signal from an average activity of the brain through the skull and reflects the massed activity of many neurons, thus leading to a limited use. While signal quality can be improved with more invasive recording where similar electrodes are placed on the dura (a protective layer of tissue covering the brain) or on the cortical surfaces of the brain, resolution is still somewhat limited.

Another approach for brain activity monitoring involves inserting an electrode (or array of electrodes) into the cerebral cortex and recording spikes and local field potentials from the cortex area. Recent advances in micro-fabrication technologies allowed for a realization of dense arrays as high as 128×128 elements that are implanted in the cortex. This electrode approach facilitates brain activity monitoring and can provide valuable information on brain activity, sensory perception and higher cortical functions. Such an electrode array has been examined as part of a "brain-machine interface" (BMI) approach to allow movement control for paralyzed patients. However, multiple neuron recordings provide a significantly more challenging decoding problem than EEG signals, both because the signal is complex and because the processing demands are large. Electrical signals obtained using this type of approach are typically digitized at high rates (typically above 20 kHz) for many channels. In addition, the signals typically need to be separated from the noise and decoding algorithms typically are needed to process neural activity into some pattern or provide useful control command signals within a meaningful time frame (e.g., on the order of 200 milliseconds). Furthermore, this invasive electrode approach involves a neurosurgical operation to install the electrodes, and the electrode lifetime is limited because the immune system slowly walls off and even rejects the electrodes.

One method of brain imaging known as Intrinsic Optical Signal (IOS) imaging is used for mapping activity patterns of the cerebral cortex. It has provided the bulk of the known functional information about the columnar architecture, one of the key features of sensory and motor cortex organization. IOS imaging is typically invasive, requiring at least an incision in the scalp and often craniotomy, but measures activity patterns with spatial resolutions below 0.1 mm. While the bulk of IOS imaging work has involved craniotomy procedures, the use of far red and NIR light allows high-resolution IOS results to be obtained through skull and intact meninges. IOS imaging is based on imaging photons reflected diffusely from a surface of live brain tissue illuminated by an external light source. This diffuse reflection is a consequence of single and multiple scattering of photons within the turbid, but only weakly absorbing, tissue of the cerebral cortex. The signals discerned by imaging this diffuse reflection are called "intrinsic" because no exogenous stains or indicator dyes are used. Fortuitously, the light scattering and absorption processes that govern the diffuse reflection vary with neural activity and thus provide useful functional information. Activity-dependent changes in diffuse reflectance have several different physical origins, including changes in the amount of hemoglobin with brain volume elements, changes in the oxygenation state of hemoglobin, and light scattering changes that are independent of hemoglobin. To date, IOS imaging systems have been implemented as bulky, fixed instruments, requiring that the subject be immobilized and, almost always anesthetized.

The above-mentioned difficulties have presented challenges to sensing and analyzing biological characteristics.

SUMMARY

The present invention is directed to sensing biological characteristics in a manner that address the aforementioned issues, as well as other related issues.

According to one example aspect of the present invention, brain activity is monitored using an emitter and detector combination respectively adapted to pass emissions into a cerebral cortex and to detect a response thereto. The emitter and detector are located at an anatomical portion of a subject that is outside of and adjacent to the cerebral cortex, with the emitter and detector substantially non-intrusively interacting with the cerebral cortex.

According to another example aspect of the present invention, an implantable integrated circuit arrangement is adapted to monitor activity of an area of a cerebral cortex that would normally be covered by an anatomical layer. The integrated circuit arrangement includes an optics circuit layer located outside the cerebral cortex area and including an emitter and a detector. The detector is adapted for sensing at least one brain-activity parameter as a function of a response of the cerebral cortex to an emission from the emitter. Such a response may include, for example, a reflective or fluorescent response. A data-processing circuit at least partially located, for example, in the integrated circuit arrangement, assimilates neural data with the detected response. With this approach, highly selective sensing of areas of a cerebral cortex is facilitated in a substantially non-invasive manner.

According to another example aspect of the present invention, an integrated circuit detection arrangement includes an emission source and at least one optical detector coupled to a substrate arranged to form a pixel, with the pixel being further arranged in a planar array of pixels. The emission source is adapted to emit a first electromagnetic radiation away from the substrate to excite a portion of a biological substance such as a cerebral cortex into emitting a second electromagnetic radiation. A filter is optically coupled to the at least one optical detector, the filter being arranged and configured to attenuate the first electromagnetic radiation from being sensed by the optical detector, thereby achieving spectral separation. Alternatively, the optical detector, or several optical detectors, are arranged and configured to discriminate the second electromagnetic radiation by parameters such as temporal lifetime or intensity. The optical detector is adapted to sense the second electromagnetic radiation and generate a detection signal in response to sensing the second electromagnetic radiation.

These above-characterized aspects, as well as other aspects, of the present invention are exemplified in a number of illustrated implementations and applications, some of which are shown in the figures and characterized in the detailed description and claims that follow. However, the above summary of the present invention is not intended to describe each illustrated embodiment or every implementation of the present invention.

BRIEF DESCRIPTION OF THE DRAWINGS

The invention may be more completely understood in consideration of the detailed description that follows in connection with the accompanying drawings, and in which.

Figure 1:
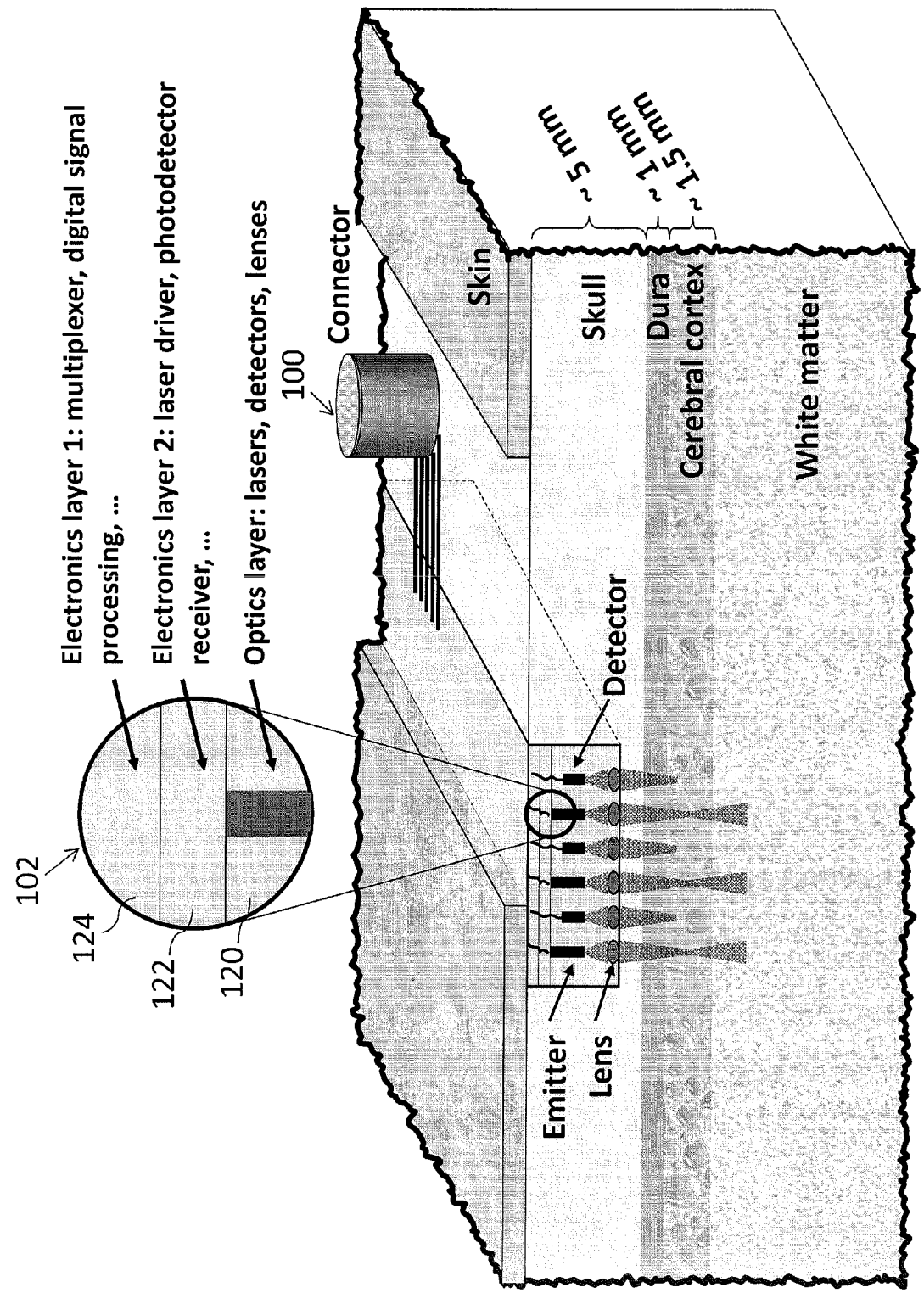
FIG. 1 shows a sensor arrangement implanted in the skull of a subject, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to a variety of different types of devices and sensing approaches. The invention has been found to be particularly suited for sensing characteristics of biological substances, such as cerebral cortex matter, with an integrated circuit arrangement adapted for emission and detection. While the present invention is not necessarily limited to such applications, various aspects of the invention may be appreciated through a discussion of various examples using this context.

One aspect of the present invention integrates optoelectronics and/or micro-optics sensing circuitry for directing an emission to a cerebral cortex and detecting a response such as reflectance or fluorescence therefrom. The response can be used for detecting or otherwise identifying characteristics of the cerebral cortex.

The integrated circuitry is located substantially immediately adjacent to the cerebral cortex in a manner that facilitates the detection of the response. For example, the circuitry can be placed on or under the scalp, on the skull or a thinned portion of the skull or embedded in the skull. In other examples the integrated circuitry is placed even closer to the cerebral cortex, such as on dura inside the skull or on the cortical surface under the dura.

In one implementation, an implantable integrated circuit includes an emission source and a detector, the emission source being implemented to emit electromagnetic radiation toward a cerebral cortex and the detector being implemented to detect a response to the emission. Such a response may include, for example, reflected and/or fluoresced radiation that can be used to form an image or other output that is recognizable or otherwise usable in the detection of characteristics of the cerebral cortex.

The integrated circuit is optionally implanted away from the cerebral cortex, such as in a portion of dura or skull over the cerebral cortex, without necessarily breaching or otherwise physically disturbing the cerebral cortex. In this regard, the integrated circuit negligibly intrudes the entity in which it is implanted (e.g., does not physically intrude the cerebral cortex and/or causes little or no response of the immune system). The emission source directs an electromagnetic emission such as light into the cerebral cortex and a response to the electromagnetic emission is detected. In one implementation, the response includes a reflected portion of the electromagnetic emission, with characteristics of the reflected portion being detected and correlated to a reflectance characteristic of the cerebral cortex. The reflectance is in turn used to detect one or more characteristics of the cerebral cortex. This reflectance-based approach is useful, for example, for detecting neural activity and related hemodynamic processes that inherently change the reflectivity coefficient ($\Delta r/r \approx 0.1\%$). In another implementation, the response includes a fluorescent response of the cerebral cortex to the electromagnetic radiation, with characteristics of the fluorescent response being detected and used to detect one or more characteristics of the cerebral cortex.

In another implementation wherein light is used by the emission source, the spectrum of the light is tailored for a particular type of response as discussed in the preceding paragraph. For instance, when a reflective characteristic of the cerebral cortex is desirably detected, the emission source uses a light wavelength that facilitates the detection of a reflected portion thereof. Similarly, when a fluorescent response is desirably detected, a wavelength of light that causes such a response is used to facilitate relatively fast neuronal signal readout.

In another implementation, the integrated circuit discussed above further includes processing circuitry adapted to control the emission source and to process the detected response. For instance, the detected response can be processed to provide an output in a particular format that can be used by a computer coupled to the integrated circuit. In addition, the processing circuitry can be used to filter out selected elements of a detected response, such as portions of an emission from the emission source, emissions of the cerebral cortex that are unrelated to the emission and/or other noise elements. With this approach, on-chip circuitry facilitates rapid processing and control of the emission source and detector while maintaining a generally negligible intrusion to the entity in which the integrated circuit is implanted.

In still another implementation, the integrated circuit discussed above includes a plurality of emission sources and detectors in an array, with each emission source and detector being implemented for garnering characteristics of a particular portion of a cerebral cortex. For example, when the emission sources and detectors are paired together in an array of such pairs, each pair is individually used to direct an emission to and detect a response from a particular portion of the cerebral cortex. Spatial resolution can be obtained by the placement (proximity) of the pairs relative to one another, with processing circuitry, filters and/or other approaches being implemented for attenuating or otherwise manipulating a detectable response to correlate detected characteristics with a particular location.

The sensing approaches discussed herein are applicable to a multitude of implementations involving the detection of characteristics of neural substances. In one implementation, brain functionality and perception is studied through brain activity monitoring in anesthetized free-behaving beings. In another implementation, brain activity is monitored in un-anesthetized free-behaving beings, facilitating analysis such as that involving comparisons between anesthetized and un-anesthetized states. These beings may range from small animal models like mice and rats to larger animal models like cats and monkeys. Research in model animals can lead to development of chronically implanted optical imaging devices in humans as well as provide a breadth of information on brain functionality. These targets can be realized in a system where a compact size, high functionality and low price can be combined with minimally invasive optical detection as proposed by this invention. Furthermore, these approaches facilitate relatively fast (e.g., less than one millisecond) temporal response, and good spatial response (e.g., between 50-100 microns). In this regard, the spatial resolution similar to that exhibited by larger systems such as fMRI is coupled with the temporal resolution of conventional EEG techniques to facilitate imaging of brain dynamics in the cellular and system neurobiology levels.

Other implementations involving one or more of the sensor approaches discussed herein include disease study and monitoring, and possible implementation in other settings susceptible to temperature and humidity instabilities. For example, specific gene expression monitoring (promoter activities) is facilitated with such a sensor approach. Long-term studies are also facilitated, with implanted chips being used to acquire data in normal settings (e.g., without requiring the monitoring to occur in a hospital or clinical setting). For instance, long-term studies of the plasticity of cortical function, during remote access periods (e.g., during space exploration or in hostile environments) and others are facilitated with this approach. Pharmaceutical or environmental neurotoxicological studies are facilitated by sensing cortical function and/or plasticity measurement.

In one implementation, one or more of the sensing approaches discussed herein are used with a brain-machine interface (BMI) device. For instance, the emission source and detector combination discussed above is optionally implemented with a neuro-prosthetic device aimed at monitoring neuronal activity that can be used to restore motor functions in severely paralyzed patients. A response of a cerebral cortex is processed (e.g., either on-chip with the detector or elsewhere) and used to control a prosthetic device, or electrically stimulate paralyzed musculature. This approach is useful, for example, in restoring voluntary motor control of limbs for patients suffering from extensive traumatic or degenerative lesions of the motor systems. For example, spinal cord injuries that damage descending orticospinal pathways or neuromuscular disorders such as amyotropic lateral sclerosis (Lou Gehrig's disease) can cause loss of motor control. However, in many such instances, the cerebral brain structures necessary to formulate and command movement are often operational, but the means to enact motor intent are gone. In this regard, this approach can be implemented for monitoring the cerebral brain structures and providing a signal for motor control in response thereto. Similarly, this approach can also be used in general for effecting other types of control, such as for regulation of cortical vasomotor and metabolic responses to neural activity.

In one particular implementation, a BMI device uses the output from a detector as discussed herein to monitor neuronal activity using intracranial recordings to sample the extra-cellular activity of a few hundred neurons in frontal and parietal cortical areas that are involved in planning arm and hand movements. The combined activity of this neuronal population is processed in real time, by a series of mathematical models designed to extract motor-control parameters from the raw brain signals. The outputs of these models are used to control the movements of a prosthetic arm that has been designed to allow the patient to enact fundamental upper limb movements. This neuro-prosthetic device is based on collecting neuronal activity data with an emission source and detector arrangement such as discussed above. Optionally, processing circuitry on a substrate including the emission source and detector interprets information from the detector for use in controlling the prosthetic arm.

In another example embodiment of the present invention, brain functions are optically imaged with near infrared (IR) spectroscopy using an emission source and detector combination implanted near (but not necessarily coupled to) a cerebral cortex. An array of emission sources and detector pairs is used to selectively analyze portions of the cerebral cortex, with spatial resolution being generally high with the implementation of small-scale, on-chip source/detector pairs. One type of emission source/detector pair that can be used in connection with this embodiment is discussed further below as well as in U.S. patent application Ser. No. 10/384,166, filed on Mar. 7, 2003 and entitled "Excitable Target Marker Detection," which is fully incorporated herein by reference. The relatively short distance (e.g., several microns) between detectors facilitates relatively high spatial resolution of a detected response from the cerebral cortex.

In one implementation that may involve a near IR spectroscopy approach as discussed above, hemodynamic characteristics of a patient are ascertained from the patient's cerebral cortex. Regional changes in cerebral blood flow and blood oxygenation level are monitored using a relationship between the local electrical activity and cerebral microcirculation. Correlation can be made between blood oxygenation in relevant areas of dorsolateral prefrontal cortex regions and cognitive effort such as attention and working memory.

In another example embodiment of the present invention, animal model brains are optically imaged using an implanted sensor arrangement as discussed herein to observe functional and/or structural organization of neuronal activities in response to a stimulus. A high spatial and temporal resolution image (e.g., about 50×50 microns) of the neuronal activity is obtained with the use of staining, voltage sensitive dyes that are introduced onto the brain surface. These dyes convert the action potential signals of the neurons into fluorescence intensity changes and allow monitoring of neuronal activity dynamics in a fast (e.g., sub-millisecond) time scale. Voltage dyes facilitate obtainable temporal and spatial resolution, and ease instrumentation demands by generating larger fractional optical signals. Fast dynamic signal tracking allows observation of the fluorescence signals that are directly proportional to the neuronal activity. These signals may be much smaller in magnitude compared with the intrinsic reflected light signal that relates to cerebral blood flow and blood oxygenation level. Image maps between dye and intrinsic signals are compared to study neural activity dynamics. Quantum dots are also used in connection with or in a manner similar to the voltage sensitive dye approach discussed above. In addition, fluorescent protein transgenic/transfection-related information and approaches are facilitated with such an approach.

In another example embodiment of the present invention, an electrode or electrodes are combined with the sensor approach discussed herein for high time resolution readout or write-in control of neural activity. For example, by implanting an electrode near or in the cerebral cortex, the electrode can be used to detect characteristics of the cerebral cortex in parallel with the detection using a sensor (e.g., optical detector) as discussed herein. With this approach, a combination of types of responses is detected.

In one implementation, such a combined approach involves wireless telemetry. A small battery (e.g., a button-style Zinc-air battery), which is carried under the skin of a subject's back provides continuous acquisition, pre-processing and standard, bluetooth-based telemetry of imagery from a sensor. Episodic control, recharging schemes, and custom electronics extend battery life over much longer time periods in certain applications.

The above combined approach further facilitates a microphotonic imaging chip used in applications involving very large numbers of units operating in parallel. Thus, applications such as screening neurologically efficacious lead compounds for drug discovery and pharmaceutical, cosmetic or environmental neurotoxicology are implemented by implanting and automatically monitoring large numbers of small animals in parallel. The long-term stability of an implantable sensor provides sensitivity in detecting subtle effects of tested compounds that might emerge only over relatively long periods of time.

Turning now to the figures, FIG. 1 shows a sensor arrangement 100 implanted into the skull portion of a subject, according to another example embodiment of the present invention. The emitters include one or more types of semiconductor-based optical emitters. For example, vertical cavity surface emitting lasers (VCSELs) or light emitting diodes (LEDs) can be used as emission sources. VCSELs can be implemented on a single substrate and having a single wavelength, or separately with separate wavelengths (e.g., with a pick-and-place approach with a flip-chip type substrate).

An array of photo-detectors is arranged to detect a response of the cerebral cortex to an emission directed thereto by the emitters. In one implementation, the photo-detectors include PIN diode detectors for application with relatively high light levels (e.g., in reflectance or bright fluorescence applications). In another implementation, the photo-detectors include avalanche photodiode (APD) detectors for application with relatively low light levels (e.g., in relatively dim fluorescence applications).

In some implementations, the components of the sensor arrangement are implemented for light wavelength of between about 0.6-0.8 microns. Optionally, the sensor arrangement is integrated into a relatively small overall package (e.g., about 5×5×0.5 mm). The sensor arrangement 100 can be surgically implanted in the skull and does not necessarily require exposing or penetrating the cerebral cortex. The emitters illuminate the cortex (shown by beams aligned with the emitters and extending by way of illustration into the white matter). Intrinsic reflectance changes and/or fluorescent responses (illustrated by beams aligned with the detectors) are detected and associated with neural activity in the subject. Information detected by the detectors is read out via a connector as shown for analysis. In some implementations, the connector employs wireless technology. In other implementations, the illustrated connector is replaced with wireless communications circuitry in a portion of the sensor shown embedded in the skull; signals communicated therewith are sent either directly to an analysis arrangement or to a wireless transceiver located elsewhere on the subject.

An array of micro-scale lenses focus and direct the light pathways for both the emitters and detectors. In one instance, one lens is used per detector, in another instance, one lens is used per emitter and in still another instance one lens is used per subgroup of emitters/detectors.

The emission wavelength is selected such that the light will pass through the thin layer of remaining skull (about 1 mm), dura (about 1 mm) and into cerebral cortex. The local reflectivity coefficient of the cerebral cortex is modulated by the level of neural activity therein. In this regard, the reflected light is monitored by the interspersed photo-detectors and used to provide an estimate of the spatio-temporal pattern of neural activity in cortex.

Various micro-optical designs can be implemented including refractive or diffractive imaging lens architectures and pixel and micro-optics spacing as low as 50 microns, allowing for high spatial resolution in some dense array applications. For example, the lenses shown in FIG. 1 and corresponding spacing therebetween are varied to achieve certain results for particular applications.

Figure 2:
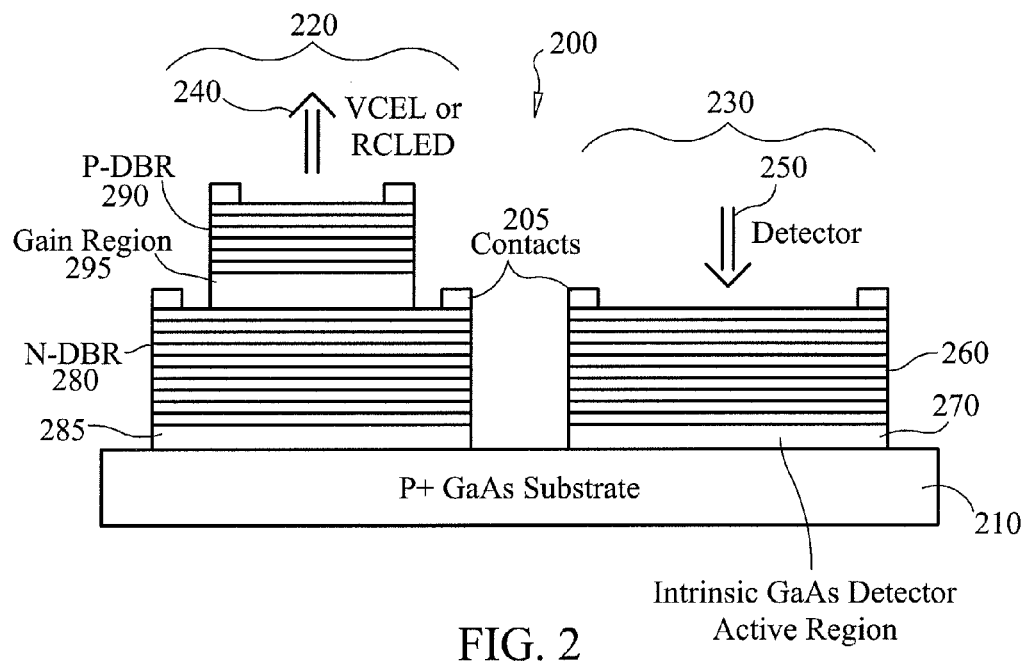
FIG. 2 shows a sensor arrangement including an emitter and a detector, according to another example embodiment of the present invention.

In one implementation, the sensor arrangement 100 combines a VCSEL or LED light source and a PIN (p-type, intrinsic, n-type) detector. One example of such detector is shown in FIG. 2 and discussed further below. An emission filter blocks the laser or LED light from reaching the detector, passing a response such as fluorescence from the cerebral cortex to the detector. Architecture for this implementation may be similar as that used for fluorescence studies of voltage sensitive dyes as discussed in D. Shoham et al., Neuron, 24, 791-802, 1999, which is fully incorporated herein by reference. When implemented for detecting intrinsic reflected signals from the cerebral cortex, this filter is removed (or not used), thus allowing the laser light to reach the detector.

Figure 3:
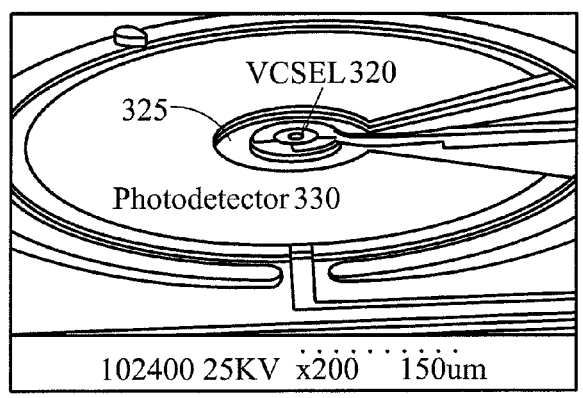
FIG. 3 shows a sensor arrangement including an emitter and a detector, according to another example embodiment of the present invention.

In another implementation, single pixel sensor unit including a VSCEL laser and detector are realized using epitaxial growth of GaAs layers using MOCVD growth technique as discussed in U.S. patent application Ser. No. 10/384,166, discussed above. An example single-pixel sensor is shown in FIG. 3 and discussed below. In one instance, the VCSEL has a lasing wavelength of about 773 nm to minimize the auto-fluorescence in living tissues while facilitating efficient signal collection of the intrinsic reflected signal. Such an approach may be implemented, for example, in a manner similar to the approach discussed in B. Chance et al., Opt. Express 2, 411-423 (1998). The power output used is related to the VCSEL laser aperture diameter and in some instances, ranges between about 0.5 and 4 mW for single mode and multi-mode laser operation respectively.

In one implementation, the emitters include lasers such as the VSCELs discussed above and are adapted for write-in control of activity in a biological specimen (e.g., in the brain) and/or for write-in production of histological fiduciary marks. For example, by applying laser light to the cerebral cortex with one (or more) of the emitters, a response can be induced in the cerebral cortex to effect these write-in control activities.

Several detection schemes such as lock-in amplification, integration of a detected signal or other processing algorithms are optionally implemented with the approach shown in FIG. 1. These schemes are tailored to extract desired features from an array of detectors while facilitating fast data processing (e.g., less than one millisecond per image frame).

In one implementation, the sensor 100 of FIG. 1 is a full imaging chip that includes layers as shown in detail in an inset 102. A lower optics layer 120 includes lasers, detectors and lenses, above which is an integrated electronics layer 122 including circuits such as laser drivers and photodetector receivers (e.g., in a CMOS flip-chip type arrangement). A top layer 124 includes additional circuitry such as a multiplexer, filter and/or a digital signal processor (DSP) for processing each sensor unit (emitter/detector pair). Other photodetection circuitry such as circuits for current-voltage (I-V) conversion, band-pass filtering, lock-in amplification and integration can also be included with the integrated electronics layer 122. The integrated electronics layer 122 also facilitates on-board signal processing based on algorithms adapted, for example, from electrode array architectures while maintaining relatively low noise operation. Data is multiplexed into an output channel and broadcast to external processing units. In one implementation involving use of the sensor 100 with a chronically implantable imaging system for motor function control of paralyzed patients, the analysis of signals in the integrated electronics layer can be directly transmitted to a prosthetic device.

The integrated electronics layer 122 is configured and arranged to control the emitters and detectors in a variety of manners, depending upon the application. In one instance, the emitters are operated such that all are on at a particular time. In another instance, the emitters are pulsed, for example using pulse lasers, to remove or reduce components of detected responses (e.g., to overcome detector dark noise).

The top layer 124 is also selectively configured for controlling the application of the emitters and detectors, or for processing responses from the detectors to achieve a variety of results. In one instance, the top layer 124 includes circuitry adapted to reduce signals to minimize downstream data transmission bottlenecks, for example using data compression (lossless or lossy). In another instance, the top layer 124 removes components of detection signals, such as laser fluctuation artifacts based on reference detectors or spatial patterns, and heartbeat or respiration artifacts. Certain desirable neural signal signatures can also be discriminated and decoded in the top layer 124. Furthermore, the top layer 124 can be implemented for managing power used by the sensor 100.

In another implementation, each emitter and detector is individually spatially addressed to establish smart patterns of "structured illuminations" involving the selective operation of a subset of emitters and corresponding detectors. With this approach, cross talk between channels (different emitters and detectors) is reduced and/or eliminated.

In one embodiment, the emitters and detectors are arranged in an array. One example array is an 8×8 array of sixty-four VCSEL lasers which are individually controlled to generate temporally structured illumination for enhanced resolution and depth discrimination. The detectors, for example, GaAs PIN diodes, are arranged in a 9×9 array surrounding the VCSEL array. Signal to noise ratios are also enhanced by heterodyning laser sources used for emitters.

In another implementation, emitter/detector pairs or subsets are selectively operated to increase temporal resolution by using sequentially smaller arrays of pixels. With this approach, more advanced processing algorithms can be developed to analyze the simultaneous activity of many neurons in the brain.

In a more particular example embodiment, the integrated electronics layer 122 is implemented with a flip chip bonded above the sensor wafer so that each sensor has a laser diode driver. The flip-chip is arranged with a circuit side including the integrated electronics layer 122 and a backside opposite the circuit side and facing the cerebral cortex (e.g., including the lenses). Each laser diode driver is implemented with modulation and amplification selected for a particular implementation. In addition, a reference signal from the laser diode is implemented for synchronization in sensitive detection applications such as lock in amplification schemes. Furthermore, control hardware and software is implemented to control which laser diode and detectors are operating at a given time. In one instance, some or all of these functions are performed externally in discrete drivers and controls coupled via the connector shown in FIG. 1. In this instance, many laser diode controllers, with modulated light options, detector transceivers and/or amplifier modules are used with a computer that controls all of the inputs and outputs.

In another particular example embodiment, the upper layer 124 facilitates the gathering of raw data from individual pixels established with emitter/detector pairs in the lower layer 120. Algorithms are implemented in the upper layer 124 with circuitry therein to make sense of and pull meaningful information from the raw data. Such algorithms may include, for example, those designed to control the collection of data and selection of emitters and detectors to be active at a particular time. For instance, breathing, respiration and pulse cycles are accounted for using such algorithms in a manner similar, e.g., to fMRI inspired algorithms.

In one instance, the upper layer 124 is implemented with algorithms that facilitate obtaining depth information from detected signals based on a particular choice of active sensor element. For more information regarding an approach for obtaining depth information, reference may be made to information available from the Photon Migration Imaging group at Harvard University.

In another instance, the upper layer 124 is implemented with algorithms for multiplexing data for an outside link for reporting characteristics (upward links) and getting information from the outside world that will influence sensor parameters (downward links). Such communications may be useful, for example, in artificial limb movement control and/or for diagnostics of disease purposes. For example, portions of a cerebral cortex exhibiting a response indicative of a particular type of disease, such as epilepsy or brain tumors, can be identified using this approach for pre-operative ambulatory or intraoperative purposes.

FIG. 2 shows a sensor 200 having an emitter 220 (emission source) and detector 230 adapted for detecting neural characteristics, according to another example embodiment of the present invention. The sensor 200 may, for example, be implemented in connection with the arrangement 100 shown in FIG. 1, with further iterations of the emitter 220 and detector 230 pair being used to form an array of the same. The sensor 200 includes a substrate 210 on which the emitter 220 and detector 230 are disposed. The detector 230 optionally includes a filter that filters undesirable light such as light emitted directly from the emitter 220. The emitter 220 and detector 230 are coupled to the substrate 210, for instance, using a scheme such as a hybrid scheme or a monolithic integration scheme. In one implementation, additional driver/processing circuitry is implemented on the substrate 210 for use in the operation of the emitter 220 and/or the detector 230.

Emitter 220 is a source of electromagnetic radiation, such as a laser or LED, designed to pass electromagnetic radiation to a cerebral cortex to cause a response such as a reflective or fluorescent response. The emitter 220 emits a first electromagnetic radiation 240 in an approximately normal direction away from the substrate 210 and toward the cerebral cortex. In response to the first electromagnetic radiation 240, the cerebral cortex exhibits a response such as fluorescence or a reflected portion of the first electromagnetic radiation 240. When the cerebral cortex exhibits fluorescence, a second electromagnetic radiation 250 is emitted therefrom, at least a portion of which is directed back toward substrate 210 where it is detected at the detector 230. In one implementation, the second electromagnetic radiation 250 has at least one detectable characteristic that is distinguishable from first electromagnetic radiation 240, for example, a different frequency from first electromagnetic radiation 240. This distinguishable characteristic can be used to filter out the first electromagnetic radiation 240 from the detector 230.

The detector 230 includes at least one optical-detector 270 (e.g., a photodiode) coupled to the substrate 210 in proximity to the emitter 220. In one implementation, light scattered and/or reflected back into the optical-detector 270 (e.g., not only from an associate light source, but also from adjacent light sources) is filtered by filter 260 to attenuate and/or block electromagnetic radiation. Other light that is filtered may include excitation light scattered from optical interfaces (e.g., micro-optics) as well as from the biological sample.

Optical-detector 270 is adapted to sense the second electromagnetic radiation 250 and, in response, to generate a detection signal (e.g., for readout by an electronic circuit arrangement, for example as shown in FIG. 1) for further processing. Optionally, filter 260 is optically coupled to (e.g., physically coupled to, or integrally formed upon) the optical-detector 270. In addition, the filter 160 may be implemented using one or more of a variety of filter types such as low-pass, high-pass and/or band-pass filters, depending upon the application and available material.

Various optical-detector technologies can be used in connection with the detector 270, including PIN, PN, metal-semiconductor-metal (MSM), photoconductivity and CCD (charged-coupled device) optical-detectors. In some implementations, the gain of the optical-detector(s) is increased to increase the sensitivity thereof. In various applications, avalanche optical-detectors (APDs), on-chip preamplifiers and/or photo-transistors are used to provide relatively higher gain to increase optical-detector sensitivity, for example, in high-bandwidth applications as discussed above. In another implementation, a resonant cavity optical-detector (RCPD) is used to filter out background electromagnetic radiation from the excitation source (i.e., high extinction).

Referring again to FIG. 2 and according to another example embodiment, emitter 220 is a micro laser such as a vertical-cavity surface-emitting laser (VCSEL) monolithically integrated along with the detector 230. The emitter structure (e.g., VCSEL epi-layer) includes two mirrors (or distributed Bragg reflector (DBR) filters) and, in one implementation, a first N-doped DBR 280 and a second P-doped DBR 290. Typical DBRs or interference filters that have been found to be beneficial for use in connection with one or more of the example embodiments discussed herein include AlGaAs DBRs that are grown to be at least 99.99% reflecting. Due to the high index of AlGaAs, the angular sensitivity of the DBR is drastically reduced. In one instance, spatial filtration is implemented in conjunction with the AlGaAs DBR filter to achieve higher sensitivity. The mirrors are separated by a quantum well, laser gain region 295. Region 285 lies between the first N-doped DBR 280 and the substrate 210 and in one implementation includes intrinsic and/or doped GaAs.

FIG. 3 shows a source/detector arrangement 300 including metal blocking layer 325 (i.e., a source filter as discussed above) placed between a VCSEL excitation source 320 and mesa photodetector 330, according to another example embodiment of the present invention. The metal blocking layer 325 is adapted to attenuate or block emissions from the VCSEL excitation source 320 from reaching the photodetector/filter 330. Specifically, the metal blocking layer 325 blocks stray emissions from the VCSEL excitation source 320 from traveling laterally toward the photodetector/filter 330. In one instance, the shape and location of the metal blocking layer 325 is selected to reflect stray emissions from the VCSEL excitation source 320 up and away from the photodetector/filter 330.

The metal blocking layer 325 extends laterally between the VCSEL excitation source 320 and the photodetector/filter 330. In addition, the metal blocking layer 325 extends above the VCSEL excitation source 320 and the photodetector/filter 330, relative to the direction of emissions from the VCSEL excitation source. The curved structure of the metal blocking layer 325, as well as the height thereof is arranged to direct emissions reflecting therefrom in a direction generally away from the photodetector/filter 330.

The various sensor arrangements, emission sources and detectors discussed herein may be formed using one or more of a variety of techniques. According to one example approach, at least one excitation/emission source is bonded onto a silicon-based platform (e.g., an integrated circuit), the platform including filters, detectors and control circuitry formed therein. In another example approach, excitation sources of different wavelengths are bonded upon a common substrate and used in applications employing multiple detection approaches for a common sample. For instance, different characteristics of a common cerebral cortex can be detected using different excitation sources that are tailored, or optimized, in wavelength for detecting a particular characteristic.

According to another example embodiment, a sensor arrangement such as that discussed herein is formed by bonding at least one emission source and corresponding silicon-based optical-detectors onto a silicon-based integrated circuit platform. In one implementation, the sensor arrangement is formed by bonding at least one emission source, corresponding optical-detectors, and any necessary electronic circuitry onto a glass, plastic or quartz platform, thereby allowing for a transparent substrate. In each of the above-mentioned approaches, an emission-specific filter is optionally integrated onto the optical-detector during fabrication of the optical-detector.

In another embodiment, the source/detector arrangement of FIG. 3 includes a monolithic fluorescence sensor with VCSELs and PIN diode photodetectors integrated on a single GaAs substrate. Both the VCSEL emitters and PIN diode detectors are adapted for operating in the NIR spectrum. In one instance, the VCSELs are implemented with a 14 μm output aperture and emit 2.5 mW with approximately 10% electrical efficiency, with implemented PIN diodes detecting at about 85% quantum efficiency with dark current below about 500 fA/mm (detector diameter) and a linear response over about 9 orders of magnitude. Using this approach, fluorescence sensitivity of the source/detector arrangement for dyes flowing in a micro-channel is estimated to be as low as 40 nMolar. Simulation using a non-sequential ray tracing program (ASAP by BRO Inc., AZ) facilitates optimization of the sensor and micro-optics performance, by the source/detector arrangement. According to another example embodiment of the present invention, fluorescence sensor components are monolithically integrated, e.g., rather than being formed independently and subsequently bonded together by some method. At least one emission source, corresponding optical-detector(s) and filter(s) are monolithically integrated on a common substrate. In some schemes, driving, readout and processing circuitry for the emitter/detector pair(s) is monolithically integrated as well.

In one implementation, the monolithically-integrated components discussed above are formed using deposition techniques including one or more of: sputtering, e-beam, evaporation, thermal evaporation, or similar deposition techniques to create layers. Thereafter, implantation and other methods are used to create regions within the layers, and etching or other means for removing portions of deposited layers are used to form a monolithic integration circuit arrangement. Also, epitaxial growth methods can be used such as molecular beam epitaxy (MBE), metal-organic chemical vapor deposition (MOCVD) and liquid phase epitaxy (LPE).

A variety of material systems are applicable for implementing particular aspects of the present invention. For example, AlGaAs is useful for forming optoelectronic components; wide band gap III-V and II-VI semiconductor materials such as ZnSe and GaInN are useful for forming visible spectrum LEDs and VCSELs; low band gap III-V and II-VI materials such as GaInNAs, InP, GaInAs, and GaInAsP are useful for extending photo detection absorption to longer wavelengths in the infrared; silicon is useful for manufacturing electronic and optical-detector components; glass/quartz substrates are useful when substrate transparency is a problem; and organic light emitting materials are useful for manufacturing certain excitation sources.

Figure 4A:
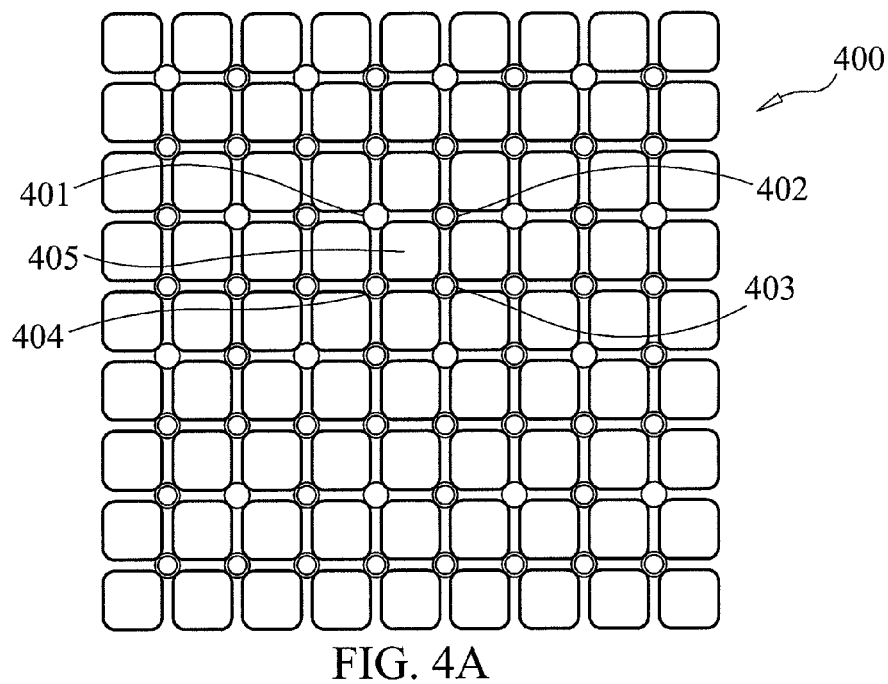
FIGS. 4A-C show a structured illumination scheme, according to another example embodiment of the present invention.
Figure 4B:
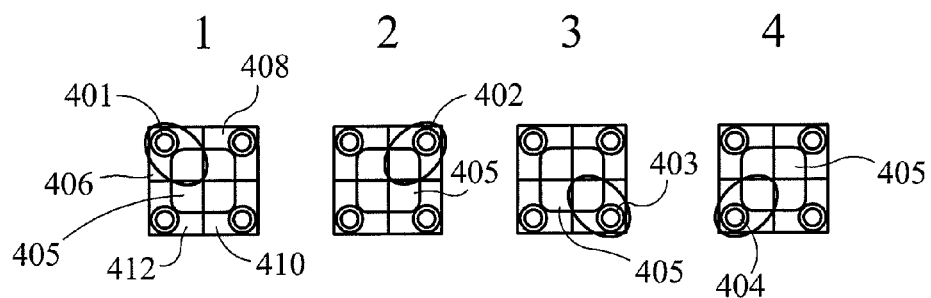
Figure 4C:
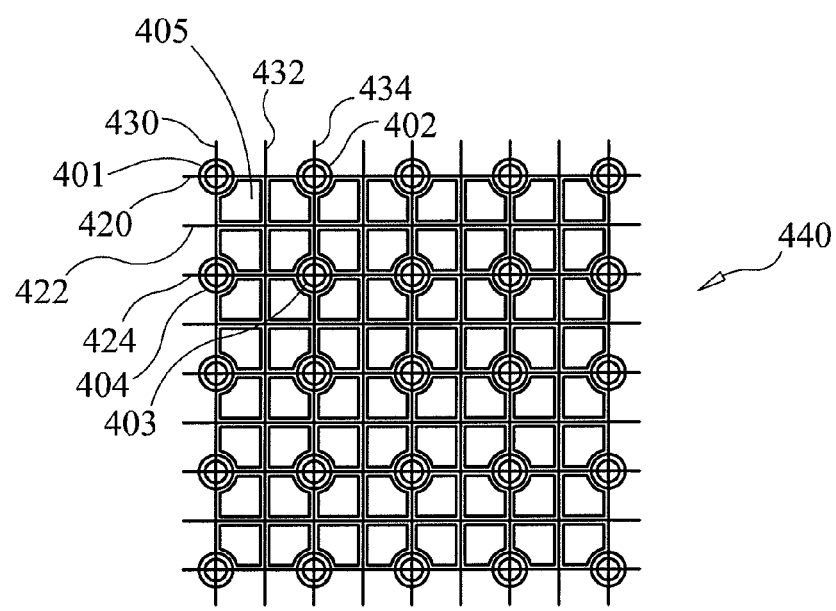

FIGS. 4A-C show structured illumination schemes for an implantable sensor, used in connection with various example embodiments. These approaches may be implemented using, e.g., four-phased structured illumination, compatible with the above-discussed GaAs device technologies. Other schemes use these hardware architectures and implement VCSEL sequences and data acquisition programs. The schemes in FIGS. 4A-4C involve detectors (e.g., PIN diodes) arranged adjacent to emitters (e.g., VCSELs) in an addressable array.

FIG. 4A shows an implantable sensor array 400 having several detectors, including detector 405, adjacent emitters including emitters 401, 402, 403 and 404. The sensor array 400 is adapted for implementing at least four phases of illumination, where one fourth of the VCSELs are active in any phase. The sensor area is tiled with units of four VCSELs (e.g., 401, 402, 403, 404) arranged at array locations around a detector (e.g., 405) in a repeating pattern.

FIG. 4B schematically illustrates an approach to a four-phase scan implemented with the array 400 in FIG. 4A, wherein lateral resolution in both horizontal and vertical directions is doubled by resolving four pixels per detector. For instance, referring again to detector 405, four pixels (406, 408, 410 and 412) are resolved and accordingly associated with the emitters (401, 402, 403 and 404). Detection by one detector (e.g., PIN diode) 405 is illustrated for each of the four numbered illumination phases (1-4), wherein emitters 401, 402, 403 and 404 are sequentially activated relative to phases 1, 2, 3 and 4, with the detector correspondingly detecting responses to each sequential emission. The slanted ovals represent a turbid medium locus that is interrogated during a particular phase. Reduction of the directions from which light would reflect onto any given detector during each phase (compared to uniform, unstructured illumination) reduces the volume of the imaged element as well as quadruples the number of pixels into which the image area is tiled. That is, relative to taking a single sample with the detector 405 upon interrogation of a local turbid medium, the detector takes four samples, each relative to the individual emitter being operated (and the corresponding pixel), thus reducing the volume of the imaged element by one-fourth.

FIG. 4C shows an addressable implementation of a sensor array, similar to the array 400 as implemented with the corresponding phases in FIG. 4B, tiled in an IOS sensor array 440 relative to the VCSEL and PIN diode layout. The array 440 includes a plurality of conductors (lines 420, 422, 424, 430, 432, and 434) that can be used to access information and control activity of components located at the intersection of the various lines.

By way of example, an emitter/detector arrangement in FIG. 4C is labeled in accordance with the approaches shown in FIGS. 4A and 4B, with a detector 405 adjacent emitters 401, 402, 403 and 404. Each of the emitters is sequentially activated via the conductors, beginning, e.g., with emitter 401 by signals applied at conductor lines 420 and 430. A response from the detector 405 is coupled via conductor lines 422 and 432. The remaining emitters are accordingly activated, with the detector 405 used to detect a response thereto.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. Such modifications and changes do not depart from the true spirit and scope of the present invention. The claims, as may be amended, added, reissued, etc., are intended to cover such modifications and devices. For example, the present invention is applicable to a variety of sensor applications and other subject matter, in addition to those discussed above. For general information regarding sensor and other implementations, and for specific information regarding approaches to which one or more of the various example embodiments and implementations discussed above may be applicable, reference may be made to the attached references set forth below. For instance, reference may be made to one or more of the following U.S. Pat. Nos. 6,272,367, 6,542,772, 5,820,558, 6,379,969, 5,914,976, 5,936,730, 5,978,401, 6,097,748, 6,197,503 and 6,344,644, and to U.S. Patent Application Publication No. US 2003/0078504 A1 for more information regarding optical electronic devices and approaches that may be applicable for implementation in connection with one or more example embodiments of the present invention. Similarly, reference may be made to one or more of U.S. Pat. Nos. 5,936,730 and 6,197,503 for more information regarding bio-sensing devices and approaches that may be applicable for implementation in connection with one or more example embodiments of the present invention. Furthermore, reference may be made to the attached Appendices A and B for additional implementation and/or applications of one or more of the various embodiments and implementations discussed herein. In this regard, each of the above patent documents is fully incorporated herein by reference.

Also, it should be appreciated that reference throughout this specification to embodiments, implementations or aspects of the invention means that a particular feature, structure or characteristic described in connection with the embodiment is included in at least one contemplated realization of the present invention. Therefore, it is emphasized and should be appreciated that two or more references to "an embodiment" or the like in various portions of this specification are not necessarily referring to the same embodiment. Furthermore, the particular features, structures or characteristics of one or more embodiments or aspects described may be combined or implemented independently of each other as suitable in one or more embodiments of the invention.

It will be apparent to one of ordinary skill in the art that aspects of the invention, as described above, may be implemented in many different forms of software, firmware, and hardware in the implementations illustrated in the figures. The actual program code or specialized signal-processing hardware used to implement aspects consistent with the present invention is not limiting of the present invention. Thus, the operation and behavior of the aspects have been described without reference to such specifics with the understanding that a person of ordinary skill in the art would be able to design and implement these described aspects based on the description herein.

What is claimed is:

1. A negligibly-intrusive method for monitoring brain activity in a cerebral cortex, the method comprising:
    displacing part of an anatomical layer adjacent the cerebral cortex with an integrated circuit having an optics layer including an emitter and an array of detectors, for directing electromagnetic radiation into the cerebral cortex,
    detecting a response of the cerebral cortex to the electromagnetic radiation and using the detected response to assimilate neural data, and wherein
    detecting a response of the cerebral cortex includes detecting a response indicative of epilepsy during an intraoperative procedure, and
    using the detected response to assimilate neural data includes using the detected response to identify a condition of epilepsy during the intraoperative procedure.

\* \* \* \* \*